(12) United States Patent
Lin

(10) Patent No.: US 6,432,140 B1
(45) Date of Patent: Aug. 13, 2002

(54) INTERVERTEBRAL RETRIEVAL DEVICE

(76) Inventor: Chih-I Lin, 14292 Spring Vista La., Chino Hills, CA (US) 91709

( * ) Notice: Subject to any disclaimer, the term of this patent is extended or adjusted under 35 U.S.C. 154(b) by 0 days.

(21) Appl. No.: 09/640,715

(22) Filed: Aug. 18, 2000

(30) Foreign Application Priority Data

Dec. 10, 1999 (TW) .......................................... 088221110

(51) Int. Cl.7 ................................................. A61F 2/44
(52) U.S. Cl. ................................ 623/17.16; 623/17.11; 606/61
(58) Field of Search .......................... 623/17.11, 17.15, 623/17.16; 606/61, 65, 59

(56) References Cited

U.S. PATENT DOCUMENTS

| | | | | |
|---|---|---|---|---|
| 4,904,261 A | * | 2/1990 | Dove et al. .................... | 623/17 |
| 5,171,279 A | * | 12/1992 | Mathews ...................... | 623/17 |
| 5,397,364 A | * | 3/1995 | Kozak et al. .................. | 623/17 |
| 6,056,749 A | * | 5/2000 | Kuslich ........................ | 606/61 |
| 6,080,158 A | * | 6/2000 | Lin .............................. | 606/61 |
| 6,106,557 A | * | 8/2000 | Robioneck et al. ............ | 623/17 |
| 6,176,882 B1 | * | 1/2001 | Biedermann et al. ..... | 623/17.15 |
| 6,206,922 B1 | * | 3/2001 | Zdeblick et al. .......... | 623/17.11 |
| 6,277,149 B1 | * | 8/2001 | Boyle et al. ............. | 623/17.16 |
| 6,306,170 B2 | * | 10/2001 | Ray ......................... | 623/17.11 |

* cited by examiner

Primary Examiner—Corrine McDermott
Assistant Examiner—Alvin Stewart
(74) Attorney, Agent, or Firm—Bacon & Thomas

(57) ABSTRACT

An intervertebral retrieval device comprises a block body and a bone nail. The block body is provided in an upper surface thereof and a lower surface thereof with a plurality of protruded teeth, with at least one of the two contact surfaces having an inclined hole. The bone nail is fastened onto a vertebra from the upper side or the lower side of a replacing intervertebral disc such that the bone nail penetrates slantingly the vertebra or its replacing body or similar device, and that the bone nail is inserted into the inclined hole of the block body.

10 Claims, 4 Drawing Sheets

INTERVERTEBRAL RETRIEVAL DEVICE

FIELD OF THE INVENTION

The present invention relates to an intervertebral retrieval device.

BACKGROUND OF THE INVENTION

The conventional intervertebral disc spacer is used in conjunction with the auxiliary fixation devices, such as the bone nail and the fixation rod, so as to prevent the disengagement of the disc spacer. The use of the auxiliary fixation devices refrain the intervertebral motion between the two vertebrae spaced by the disc spacer. In addition, the auxiliary fixation devices are not effective in averting the disengagement of the disc spacer with the vertebrae.

It is the primary objective of the present invetention to provide an intervertebral retrieval device free from the drawbacks of the prior art devices described above.

It is another objective of the present invention to provide an intervertebral retrieval device comprising a block body having an inclined hole, and a bone nail.

It is another further objective of the present invention to provide an intervertebral retrieval device comprising a plurality of block bodies and bone nails. The device of the present invention is used in conjunction with the auxiliary fixation device.

SUMMARY OF THE INVENTION

The present invention provides an intervertebral retrieval device comprising a block body provided on an upper surface and a lower surface thereof with a plurality of protruded teeth, and with an inclined hole at at least one of said upper surface and lower surface; and a bone nail fastened onto a vertebra contacting the upper surface or the lower surface of said block body with a portion of the bone nail inserting into said inclined hole of said block body.

In spite of the use of the device of the present invention in conjunction with the auxiliary fixation device, the intervertebral retrieval device of the present invention allows a relatively greater freedom of intervertebral movement between the vertebrae. This is due to the fact that the bone nail and the inclined hole of the block body of the present invention are not joined together intimately. In light of the bone nail being fastened onto the vertebra, the block body and the vertebrae are fused together.

DETAILED DESCRIPTION OF THE EMBODIMENTS

The intervertebral retrieval device of the present invention comprises a block body and a bone nail.

The block body is provided in the upper surface thereof and the lower surface thereof with a plurality of protruded teeth, and with an inclined hole at at least one of the upper and lower surfaces.

The bone nail is fastened onto an upper vertebra or a lower vertebra contacting said block body, such that the bone nail penetrates slantingly the upper vertebra or the lower vertebra, and that the bone nail is then received in the inclined hole of the block body. The upper vertebra or the lower vertebra onto which the bone nail is fastened can also be a replacing body or similar device of a vertebra.

The block body may be of any shape. The upper surface and the lower surface of the block body are a convex surface. In this specification, the "convex surface" of the block body means the surface protruded outwardly and in an arcuate manner at the portion between the ends of the block body. In this specification, the words, such as upper, lower, front, rear, left, right, refer to the upper side, the lower side, the front side, the rear side, the left side, and the right side of a human body in which the block body is implanted. The protruded teeth of the present invention can be any kinds protruded teeth known in the art, for examples random or regular cones, and parallel lateral teeth, and preferably parallel lateral teeth. The inclined hole means inclination from the upright position. Preferably, said upper surface and said lower surface of said block body each has an inclined hole.

The bone nail of the present invention is the prior art bone nail.

The bone nail may be additionally fastened onto an auxiliary vertebral fixation device.

The bone nail may be fixedly received (such as threaded) in the inclined hole of the block body. The bone nail may be inserted into the inclined hole of the block body such that the bone nail is not substantially connected with the inner wall of the inclined hole of the block body.

It is preferable that the bone nail is not fixedly received in the inclined hole of the block body, so as to allow a greater micromotion between the block body and the bone nail (the vertebrae), thereby promoting the bone ingrowth. In light of the bone nail being inserted slantingly into the inclined hole of the block body, the block body can be pulled out in the direction consistent with the inclination of the inclined hole of the block body. However, the block body is not allowed to move in this direction by the vertebrae. In other words, the block body will not slip out the bone nail, even though the bone nail and the inclined hole of the block body are not substantially joined together.

Figure 2:
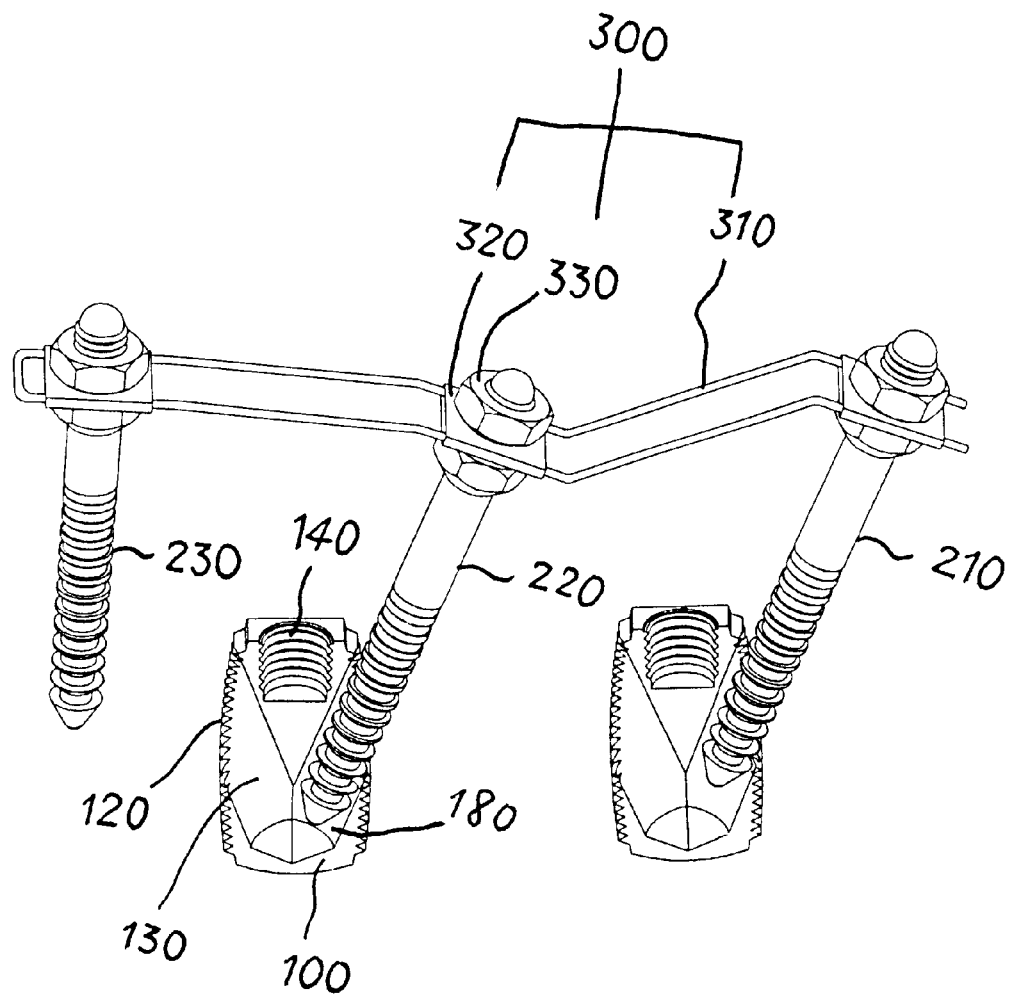
FIG. 2 shows a schematic partial cross sectional view of the present invention comprising two block bodies, three bone nails, and the auxiliary fixation device.
Figure 3:
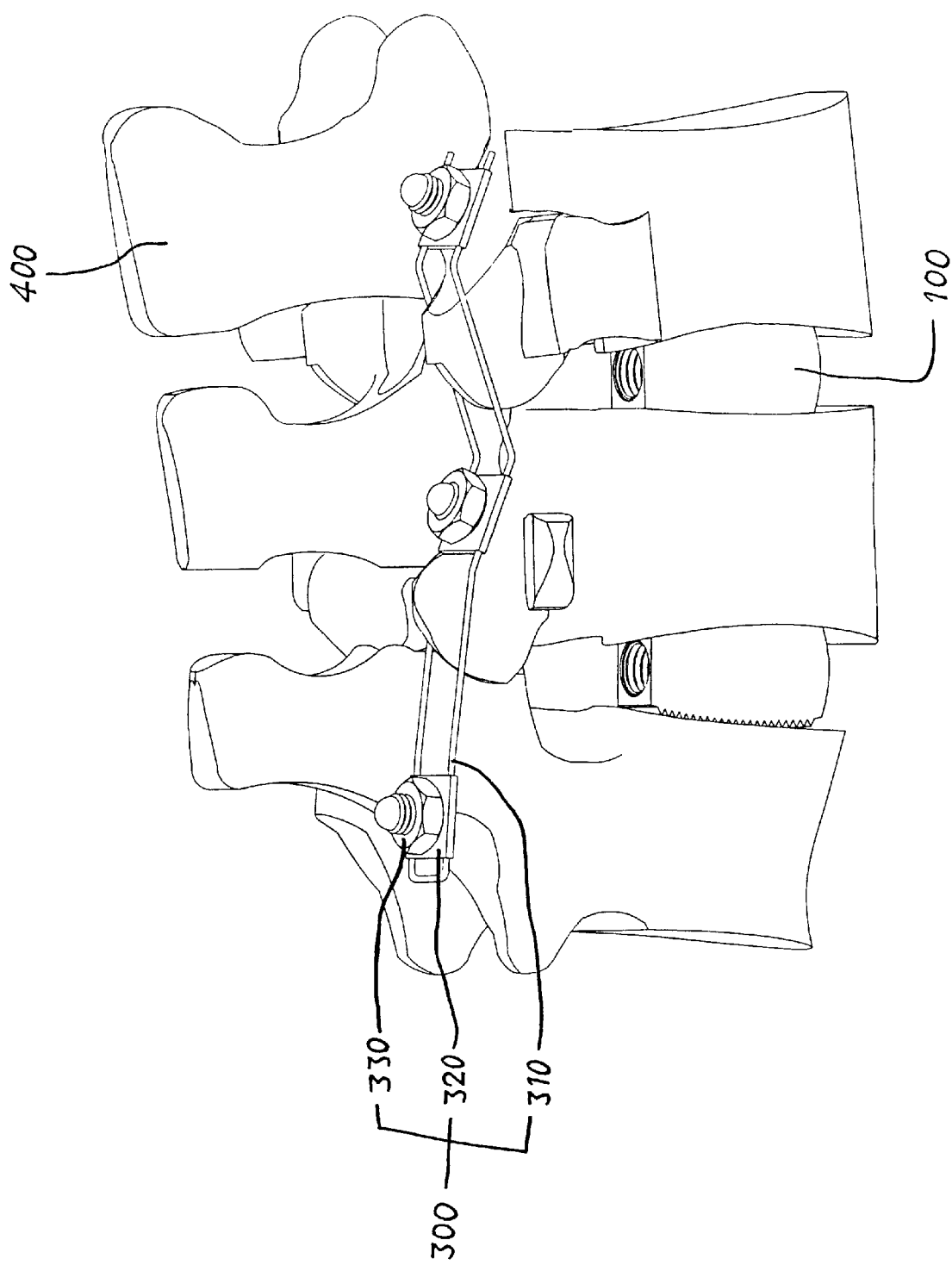
FIG. 3 shows a schematic view of the intervertebral retrieval devices of the present invention as shown in FIG. 2 implanted in a spine.
Figure 4:
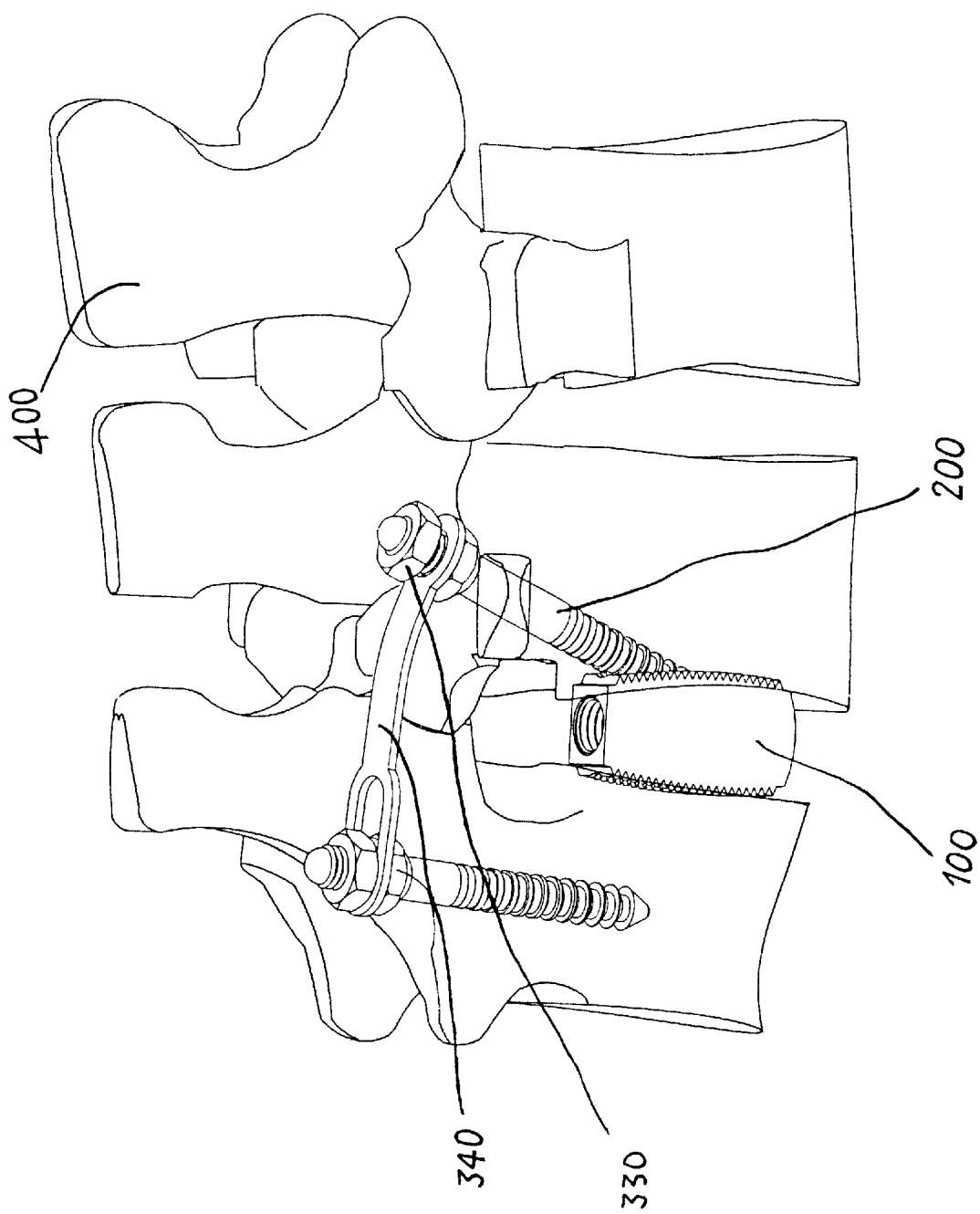
FIG. 4 shows a schematic view of the intervertebral retrieval device of the present invention being used to replace a single deformed intervertebral disc.

The intervertebral retrieval device of the present invention may be assisted by the auxiliary fixation device of the prior art, such as the auxiliary fixation device formed of an auxiliary fixation plate and auxiliary fixation screw nuts, as shown in FIG. 4, or the auxiliary fixation device formed of an auxiliary fixation thread/auxiliary fixation pieces/ auxiliary fixation screw nuts, as shown in FIGS. 2 and 3.

The block body, the bone nail and the auxiliary device of the present invention are made of biomaterials compatible biologically with the orthopedic surgery, such as stainless 316LVM, Ti-6-4, the cobaltmolybdenum-nickel alloy, etc.

The aforementioned block body comprises at least one inclined hole, preferably two inclined holes symmetrical and opposite to each other. The inclined hole is located anywhere in the upper or lower surface of the block body such that the inclined hole extends inwardly. The inclined hole is preferably located at the center of the upper or lower surface of the block body.

The present invention will be more readily understood upon a thoughtful deliberation of the following description of a preferred embodiment with reference to the accompanying drawings.

Figure 1:
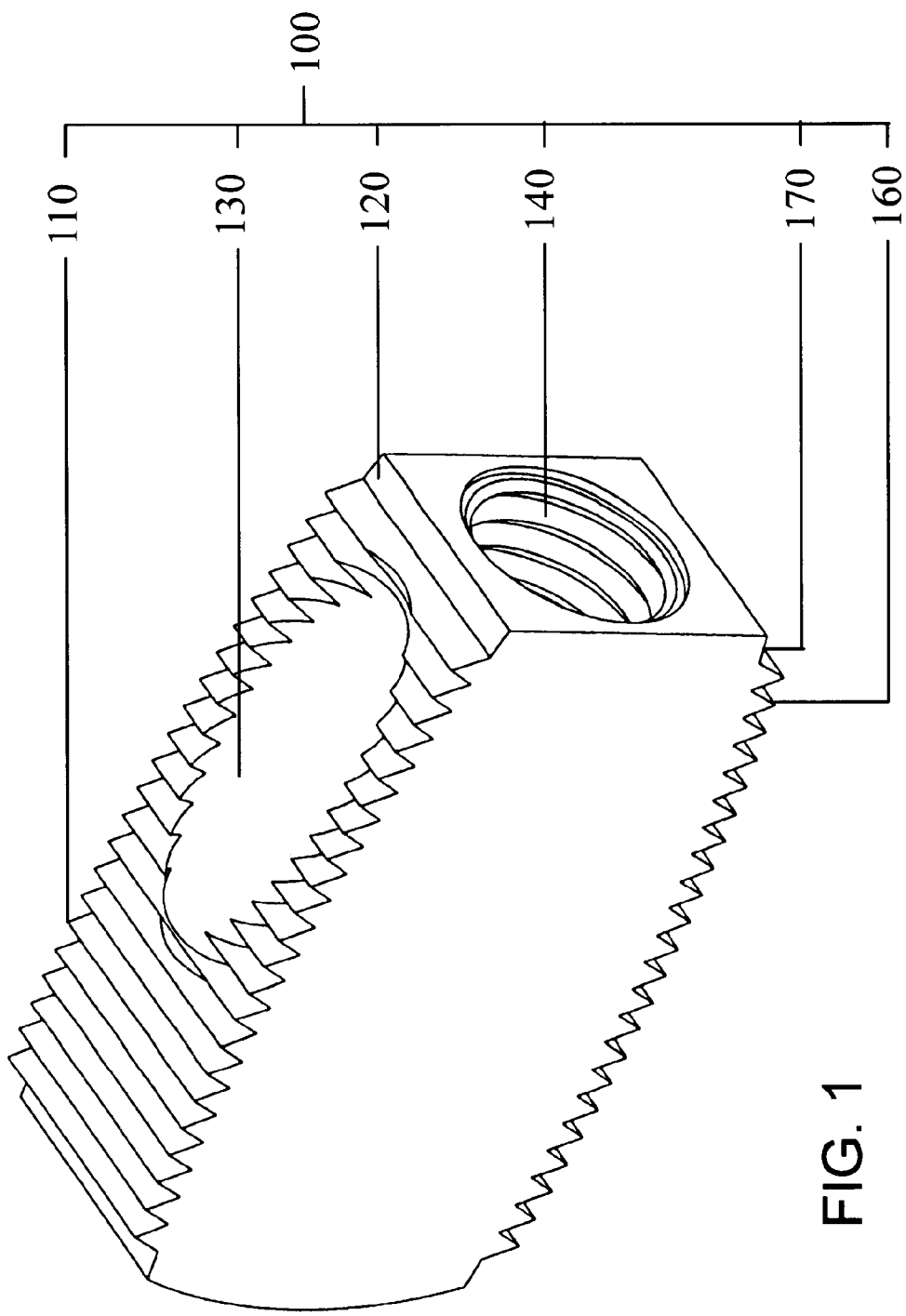
FIG. 1 shows a perspective view of a block body of the intervertebral retrieval device of the present invention.

In FIG. 1, the block body 100 has the upper surface 120, the protruded teeth 110, and the inclined hole 130, the protruded teeth 160, the lower surface 170, and the tool hole 140. The protruded teeth 110 and 160 are formed of stripe-shaped teeth parallel to one another. The inclined hole 130 is devoid of threads.

In FIG. 2, the reference numerals of 100, 110, 120, 130, 140, 160, 170 are similar in definition to those in FIG. 1. The lower surface of the block body 100 has an inclined hole 180. Tails of bone nails 210, 220, and 230 to be fixed onto vertebrae are received in the inclined holes of the block bodies after being fastened to an auxiliary fixation device comprising a fixation thread 310, and three fixation pieces 320, and three fixation screw nuts 330. As shown in FIG. 2, only a portion of the bone nails are inserted into the inclined hole of the block body. FIG. 2 also shows an embodiment of the invention wherein the inclined hole does not pass completely through the block body so that the inclined hole has only one opening.

FIG. 3 is a schematic view of two deformed intervertebral discs being fixed by two sets of the intervertebral retrieval devices of FIG. 2, wherein only one set is shown in the drawing. The reference numerals 100, 300, 310, 320, and 330 are similar in definition to those in FIG. 2. The reference numeral 400 refers to vertebrae.

In FIG. 4, the auxiliary fixation device 300 comprises a fixation plate 340 and a fixation screw nut 330. The reference numerals 100, 200, and 400 are similar in definition to those of FIG. 3.

What is claimed is:

1. An intervertebral retrieval device comprising
   a block body provided on an upper surface and a lower surface thereof with a plurality of protruded teeth, and with an inclined hole at at least one of said upper surface and lower surface;
   a bone nail to be fastened onto a vertebra contacting the upper surface or the lower surface of said block body with only a portion of the bone nail inserting into said inclined hole of said block body; and
   wherein said inclined hole does not pass comletely through the block body so that the inclined hole has only one opening.

2. The intervertebral retrieval device as defined in claim 1, wherein said upper surface and said lower surface are a convex surface.

3. The intervertebral retrieval device as defined in claim 2, wherein said protruded teeth of said block body are parallel lateral teeth.

4. The intervertebral retrieval device as defined in claim 1, wherein said upper surface and said lower surface of said block body each has an inclined hole.

5. The device of claim 1 wherein said portion of the bone nail in said inclined hole is not fixedly received in the inclined hole.

6. An intervertebral retrieval device comprising:
   a plurality of block bodies, each of which is provided on an upper surface and a lower surface thereof with a plurality of protruded teeth, and with an inclined hole at at least one of said upper surface and lower surface;
   a plurality of bone nails, each of which is to be fastened onto a vertebra contacting the upper surface or the lower surface of said block body with only a portion of the bone nail inserting into said inclined hole of said block body;
   an auxiliary fixation device enabling said bone nails to join together; and
   wherein said inclined hole does not pass completely through the block body so that the inclined hole has only one opening.

7. The intervertebral retrieval device as defined in claim 6, wherein said upper surface and said lower surface are a convex surface.

8. The intervertebral retrieval device as defined in claim 7, wherein said protruded teeth of said block body are parallel lateral teeth.

9. The intervertebral retrieval device as defined in claim 6, wherein said upper surface and said lower surface of said block body each has an inclined hole.

10. The device of claim 6 wherein said portion of the bone nail in said inclined hole is not fixedly received in the inclined hole.

* * * * *